United States Patent
Monkawa et al.

(10) Patent No.: US 10,520,453 B2
(45) Date of Patent: Dec. 31, 2019

(54) IMAGE ACQUISITION DEVICE, IMAGE ACQUISITION METHOD, AND IMAGE CORRECTION PROGRAM

(71) Applicant: Tokyo Metropolitan Industrial Technology Research Institute, Tokyo (JP)

(72) Inventors: Akira Monkawa, Tokyo (JP); Shoichi Nakanishi, Tokyo (JP); Shinya Abe, Tokyo (JP)

(73) Assignee: Tokyo Metropolitan Industrial Technology Research Institute, Tokyo (JP)

( * ) Notice: Subject to any disclaimer, the term of this patent is extended or adjusted under 35 U.S.C. 154(b) by 119 days.

(21) Appl. No.: 15/579,672

(22) PCT Filed: Jun. 3, 2016

(86) PCT No.: PCT/JP2016/066539
§ 371 (c)(1),
(2) Date: Dec. 5, 2017

(87) PCT Pub. No.: WO2016/195058
PCT Pub. Date: Dec. 8, 2016

(65) Prior Publication Data
US 2018/0172606 A1    Jun. 21, 2018

(30) Foreign Application Priority Data

Jun. 5, 2015   (JP) .................................. 2015-115101

(51) Int. Cl.
*A61B 6/00*     (2006.01)
*G01N 23/046*   (2018.01)
*A61B 6/03*     (2006.01)

(52) U.S. Cl.
CPC ........... *G01N 23/046* (2013.01); *A61B 6/032* (2013.01); *A61B 6/4021* (2013.01); *A61B 6/469* (2013.01);
(Continued)

(58) Field of Classification Search
CPC ....... A61B 6/032; A61B 6/4021; A61B 6/469; G01N 23/046; G01N 2223/20;
(Continued)

(56) References Cited

U.S. PATENT DOCUMENTS 7,840,249 B2     11/2010 Wang et al.
9,237,874 B2 *   1/2016 DeMan ................. A61B 6/032
(Continued)

FOREIGN PATENT DOCUMENTS

EP   1380263 A1   1/2004
EP   1531426 A1   5/2005
(Continued)

OTHER PUBLICATIONS

D.S. Lalush, "Feasibility of transmission micro-CT with two fan-beam sources," 2004, Proceedings of the 26th Annual International Conference of the IEEE EMBS, pp. 1283-1286. (Year: 2004).*
(Continued)

*Primary Examiner* — Kiho Kim
(74) *Attorney, Agent, or Firm* — Sheppard, Mullin, Richter & Hampton LLP

(57) ABSTRACT

Provided are an image acquisition device and an image acquisition method capable of acquiring the internal and external contours of a measured object with a high degree of accuracy. An image acquisition device 1 includes: a first X-ray source 10 that applies X-rays having a first focal point size; a first detector 20 that detects X-rays applied from the first X-ray source 10 and having passed through a measured object O; a first image generation means 30 that generates a
(Continued)

first X-ray CT image on the basis of the X-rays detected by the first detector 20; a second X-ray source 40 that applies X-rays having a second focal point size smaller than the first focal point size; a second detector 50 that detects X-rays applied from the second X-ray source and having passed through the measured object O; a second image generation means 60 that generates a second X-ray CT image on the basis of the X-rays detected by the second detector 50; and an image correction means 70 that corrects the first X-ray CT image generated by the first image generation means 30 on the basis of the second X-ray CT image generated by the second image generation means 60.

6 Claims, 10 Drawing Sheets

(52) U.S. Cl.
CPC ... *G01N 2223/20* (2013.01); *G01N 2223/419* (2013.01); *G01N 2223/42* (2013.01)

(58) Field of Classification Search
CPC ..... G01N 2223/3305; G01N 2223/401; G01N 2223/419; G01N 2223/42; G01N 2223/645; G06T 11/005
See application file for complete search history.

(56) References Cited

U.S. PATENT DOCUMENTS

| | | | |
|---|---|---|---|
| 2002/0044631 A1 | 4/2002 | Graumann et al. | |
| 2004/0234025 A1 | 11/2004 | Schroeder et al. | |
| 2005/0123089 A1 | 6/2005 | De Man | |
| 2006/0002504 A1 | 1/2006 | De Man et al. | |
| 2006/0093082 A1 | 5/2006 | Numata et al. | |
| 2009/0310736 A1 | 12/2009 | Ziegler et al. | |
| 2013/0284939 A1 | 10/2013 | DeMan et al. | |
| 2013/0287175 A1 | 10/2013 | Nagai | |
| 2015/0238159 A1* | 8/2015 | Al Assad | A61B 6/5258 378/5 |

FOREIGN PATENT DOCUMENTS

| | | |
|---|---|---|
| EP | 1612734 A | 4/2006 |
| EP | 1933170 A1 | 6/2008 |
| JP | H03108645 A | 5/1991 |
| JP | H07231888 A | 9/1995 |
| JP | H11281747 A | 10/1999 |
| JP | 2004294287 A | 10/2004 |
| JP | 2005292047 A | 10/2005 |
| JP | 2006017714 A1 | 1/2006 |
| JP | 2006125960 A | 5/2006 |
| JP | 2006329917 A | 12/2006 |
| JP | 2008070219 A | 3/2008 |
| JP | 2009543603 A1 | 12/2009 |
| JP | 2011122930 A | 6/2011 |

OTHER PUBLICATIONS

International Application No. PCT/JP2014/064330, International Search Report dated Sep. 2, 2014.
Kuang, Yu et al., "Development of XFCT Imaging Strategy for Monitoring the Spatial Distribution of Platinum-based Chemodrugs: Instrumentation and Phantom Validation," Medical Physics, vol. 40, No. 3, Mar. 2013.
Lange, Kenneth et al., "EM Reconstruction Algorithms for Emission and Transmission Tomography," Journal of Computer Assisted Tomography, New York, NY, vol. 8, No. 2, pp. 306-316, Apr. 1984.
Nishihata, Takahiro et al., "Sinogram-based Beam Hardening Correction using Volume Conservation for Single-material Objects," The Japan Society for Precision Engineering Autumn Meeting, Sep. 2012.
Suzuki, Shigehito, "Various Methods of Iterative Least-Squares Image Reconstruction for Emission Tomography," Japanese Journal of Medical Physics, vol. 19, No. 3, pp. 193-204, Sep. 30, 1999.

\* cited by examiner

IMAGE ACQUISITION DEVICE, IMAGE ACQUISITION METHOD, AND IMAGE CORRECTION PROGRAM

CROSS-REFERENCE TO RELATED APPLICATIONS

This application is a national stage application pursuant to 35 U.S.C. § 371 of International Application No. PCT/JP2016/066539 filed Jun. 3, 2016, which claims priority to Japanese Patent Application No. 2015-115101 filed Jun. 5, 2015, the disclosures of which are hereby incorporated by reference herein.

TECHNICAL FIELD

The present invention relates to an image acquisition device, an image acquisition method, and an image correction program.

BACKGROUND ART

An X-ray CT device is capable of acquiring a three-dimensional image including an internal structure of an object by carrying out reconstruction processing on an image of the object taken with X-rays from various directions. Conventionally, the features of the X-ray CT device have been used to observe minute internal defects, such as a void and a crack, in a metal part or a resin part, to measure the complicated internal shape of an electronic part, and to analyze a cause of a failure (refer to Patent Documents 1 to 4, for example).

In the present, with the advance of digital technologies, an attempt to use an X-ray CT device as the core of a digital engineering system has begun. The digital engineering system is a technology for integrating a sophisticated CAD/CAM system, a three-dimensional formative system, and a three-dimensional measurement system to achieve efficiency and high quality throughout the whole process from development to manufacturing. In order to develop products with high quality, high performance, and high reliability at low cost, it is necessary to utilize the digital engineering system from the upstream stage of design. This system can be used on a computer from the construction of a digital model to various simulations and is capable of developing products without performing various performance tests using actual models in principle. Particularly, a simulation is a useful tool to check whether a proposed design satisfies the required performance in a detailed design.

Note that, however, even if CAD were used for the design, there is no guarantee that the products have exactly the same shape when those have been made. Parts manufactured by casting, pressing, extrusion molding or the like using a die or a mold often differ from those on a design drawing in details. Practically, the products have not yet been evaluated in quality, performance, and reliability only by simulations. Therefore, in recent years, reverse engineering, in which design values are compared with values of an actual product, has been developed. The X-ray CT device is able to acquire a three-dimensional image including the internal structure of an object by reconstructing an image taken by shooting the object with X-rays from various directions and can be used for a comparison with a CAD drawing and for various structure analyses by directly modeling the image.

CITATION LIST

Patent Document

Patent Document 1: Japanese Patent Application Laid-Open No. 2006-125960
Patent Document 2: Japanese Patent Application Laid-Open No. 2006-329917
Patent Document 3: Japanese Patent Application Laid-Open No. 2008-70219
Patent Document 4: Japanese Patent Application Laid-Open No. 11-281747

SUMMARY

Technical Problem

The three-dimensional modeling using the X-ray CT device, however, has a problem that the method of deciding a threshold value between dissimilar materials or between an object and air significantly affects the dimensional accuracy of the image. The CT image is composed of cubes called "multiple voxels." Thereby, the dimensional accuracy is less affected in the case of representing a cube, while it is largely affected in the case of representing the curved surface of a sphere or the like. The voxel size depends on the X-ray focal point size and the number of pixels of a detector. In order to increase the measurement accuracy, it is necessary to increase the physical performances of the X-ray focal point size and the number of pixels of the detector.

In order to increase the physical performances of the X-ray focal point size and the number of pixels of the detector, however, there are the problems described below. Generally, the X-rays are generated by applying an electron beam to a target. The focal point size can be reduced by narrowing the electron beam. In that case, however, it is impossible to increase the tube voltage and the tube current and therefore the transmission capability is low, which hinders the internal observation. Furthermore, even if the detector is a semiconductor integrated flat panel having the highest resolution, the pixel size is 100 μm. This is because the X-rays having passed through a sample are mixed from various directions and thus it is difficult to increase the pixel size furthermore. Although it is necessary to increase the resolution of the projected image which is the base of the CT image for high-accuracy measurement, a detector capable of adequately deciding the edge of the sample is not present under the present circumstances. In order to solve the above problems, practically a three-dimensional image is created by using a gray-level gradient method in which the inclination of the surface in the voxel position is obtained from a difference between the surrounding CT values.

In the gray-level gradient method, however, the accuracy of an image depends on how many voxels are used for calculation. Since the X-ray source or the detector has a limitation in performance in the actual measurement, the number of voxels used for creating the three-dimensional image is short for satisfying the required accuracy of the image. Therefore, the edges of the obtained image are unclear, which has been a significant error cause in three-dimensional modeling creation.

An object of the present invention is to provide an image acquisition device and an image acquisition method capable of acquiring the internal and external contours of a measured object with a high degree of accuracy.

Solution to Problem

In order to achieve the objects, the present invention provides an image acquisition device including: a first X-ray source that applies X-rays having a first focal point size; a first detector that detects X-rays applied from the first X-ray source and having passed through a measured object; a first image generation means that generates a first X-ray CT image, based on the X-rays detected by the first detector; a second X-ray source that applies X-rays having a second focal point size smaller than the first focal point size; a second detector that detects the X-rays applied from the second X-ray source and having passed through the measured object; a second image generation means that generates a second X-ray CT image, based on the X-rays detected by the second detector; and an image correction means that corrects the first X-ray CT image generated by the first image generation means, based on the second X-ray CT image generated by the second image generation means.

Furthermore, the present invention provides an image acquisition method including: a first detection step of detecting X-rays applied from a first X-ray source, which applies X-rays having a first focal point size, and having passed through a measured object; a first image generation step of generating a first X-ray CT image, based on the X-rays detected in the first detection step; a second detection step of detecting X-rays applied from a second X-ray source, which applies X-rays having a second focal point size smaller than the first focal point size, and having passed through the measured object; a second image generation step of generating a second X-ray CT image, based on the X-rays detected in the second detection step; and an image correction step of correcting the first X-ray CT image generated in the first image generation step, based on the second X-ray CT image generated in the second image generation step.

Furthermore, the present invention provides an image correction program causing a computer to perform an image correction step of correcting a first X-ray CT image generated based on X-rays applied from a first X-ray source, which applies X-rays having a first focal point size, and having passed through a measured object, based on a second X-ray CT image generated based on X-rays applied from a second X-ray source, which applies X-rays having a second focal point size smaller than the first focal point size, and having passed through the measured object.

DESCRIPTION OF EMBODIMENTS

First Embodiment

To begin with, a first embodiment of the present invention will be described by using FIGS. 1 to 6.

Figure 1:
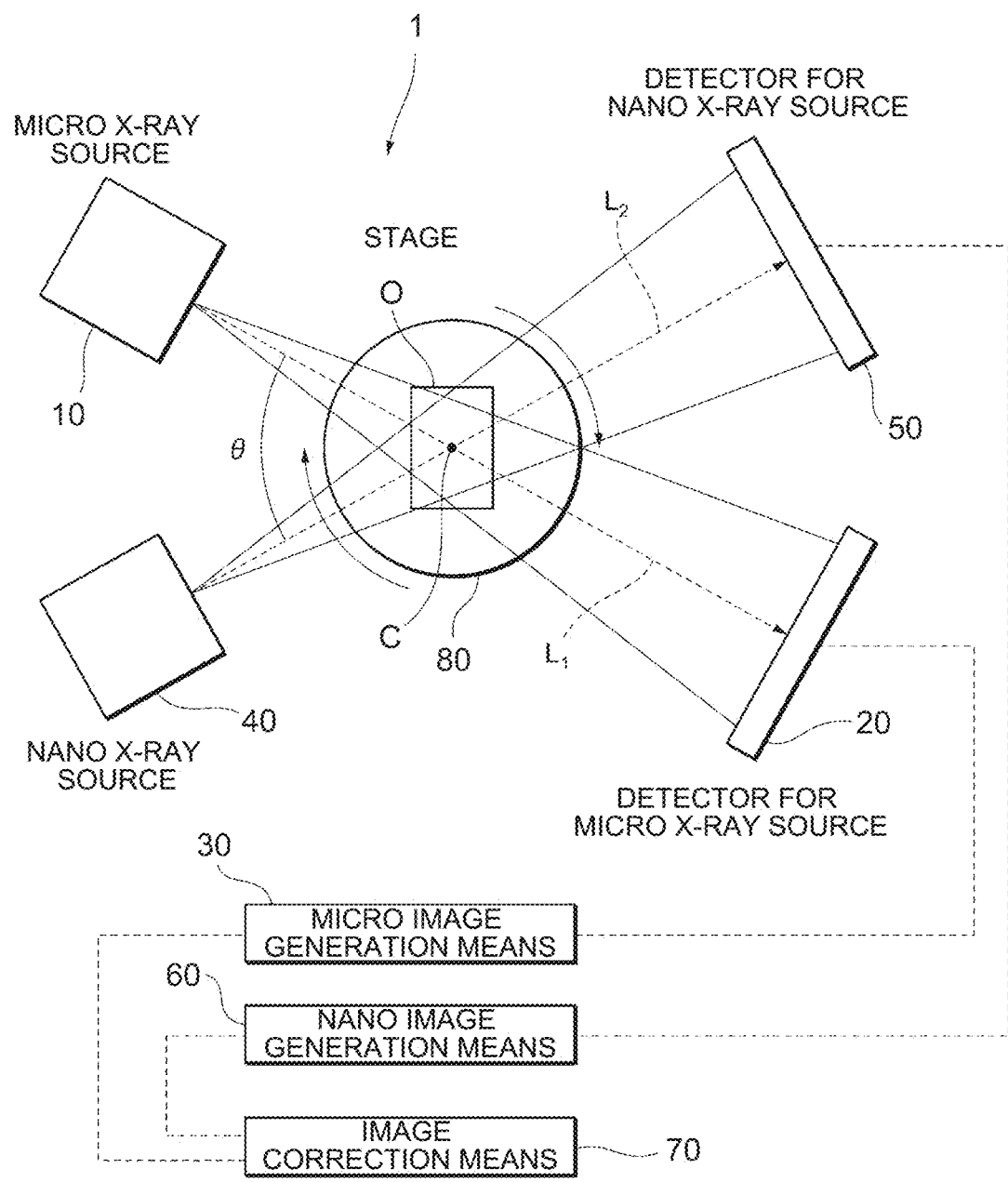
FIG. 1 is a configuration diagram for describing the configuration of an image acquisition device according to a first embodiment of the present invention.

First, using FIG. 1, the configuration of an image acquisition device 1 according to the first embodiment of the present invention will be described by using FIG. 1. The image acquisition device 1 is configured to detect projection data for each rotation angle of a measured object O by applying X-rays to the measured object O to acquire an X-ray CT image of the measured object O on predetermined three-dimensional coordinate axes. As illustrated in FIG. 1, the image acquisition device 1 includes a micro X-ray source 10, a detector for the micro X-ray source 20, a micro image generation means 30, a nano X-ray source 40, a detector for the nano X-ray source 50, a nano image generation means 60, an image correction means 70, a stage (mounting table) 80 for use in placing a measured object O.

The micro X-ray source 10 applies X-rays having a focal point size of 1 μm to 1 mm (a first focal point size) and corresponds to the first X-ray source of the present invention. The detector for the micro X-ray source 20 detects X-rays, which are applied from the micro X-ray source 10 and have passed through the measured object O, and corresponds to the first detector of the present invention. The nano X-ray source 40 applies X-rays having a focal point size of 1 to 800 nm (a second focal point size smaller than the first focal point size) and corresponds to the second X-ray source of the present invention. The detector for the nano X-ray source 50 detects X-rays, which are applied from the nano X-ray source 40 and have passed through the measured object O, and corresponds to the second detector of the present invention. As the detector for the micro X-ray source 20 and the detector for the nano X-ray source 50, a flat panel detector, a CdTe detector, or the like may be used.

The micro image generation means 30 generates a micro X-ray source image (a first X-ray CT image) on the basis of X-rays detected by the detector for the micro X-ray source 20 and corresponds to the first image generation means of the present invention. The nano image generation means 60 generates a nano X-ray source image (a second X-ray CT image) on the basis of the X-rays detected by the detector for the nano X-ray source 50 and corresponds to the second image generation means of the present invention. The micro image generation means 30 and the nano image generation means 60 of this embodiment each have a signal processing means, which quantifies the X-ray dose (X-ray peak) measured by a detector (the detector for the micro X-ray source 20 or the detector for the nano X-ray source 50), and an image reconstruction means, which reconstructs an image on the basis of numerical data obtained by the signal processing means.

The signal processing means and the image reconstruction means are each constructed by hardware such as a computer and software such as programs installed therein. Specifically, after programs for the signal processing means and for the image reconstruction means are read into a computer via a communication medium such as the Internet or a recording medium such as a USB, various kinds of processing is performed by an arithmetic processing unit such as a CPU, a storage unit such as a memory, and the like. Various data and result data required for the execution are appropriately input via an input unit or a communication unit and then output via an output unit or a display unit (for example, a display screen). Although it is described that the image reconstruction means reconstructs the X-ray CT image of the measured object O on the basis of numerical data of a detected X-ray dose by using a maximum likelihood estimation and expectation maximization reconstruction method (hereinafter, referred to as "ML-EM reconstruction method") among the successive approximation reconstruction methods, similarly to a correction means described later, the image reconstruction means is also able to reconstruct the image by using other algorithms (for example, a filtered back projection method, an addition type ART method, a multiplication type ART method, a SIRT method, a gradient method, a steepest descent method, a conjugate gradient method, a MAP-EM method, a convex method, or the like).

The image correction means 70 corrects the micro X-ray source image generated by the micro image generation means 30 on the basis of the nano X-ray source image generated by the nano image generation means 60. The image correction means 70 according to this embodiment includes a display means, which displays data of the micro X-ray source image generated by the micro image generation means 30 and data of the nano X-ray source image generated by the nano image generation means 60 as sinograms on the display screen, and a correction means, which corrects the micro X-ray source image by reconstructing the image by using the ML-EM reconstruction method among the successive approximation reconstruction methods so as to converge the sinogram of the micro X-ray source image to the sinogram of the nano X-ray source image. The display means and the correction means are each constructed by hardware such as a computer and software such as programs installed therein. After programs for the display means and the correction means are read into the computer, various kinds of processing is performed by an arithmetic processing unit such as a CPU, a storage unit such as a memory, and the like.

Figure 2:
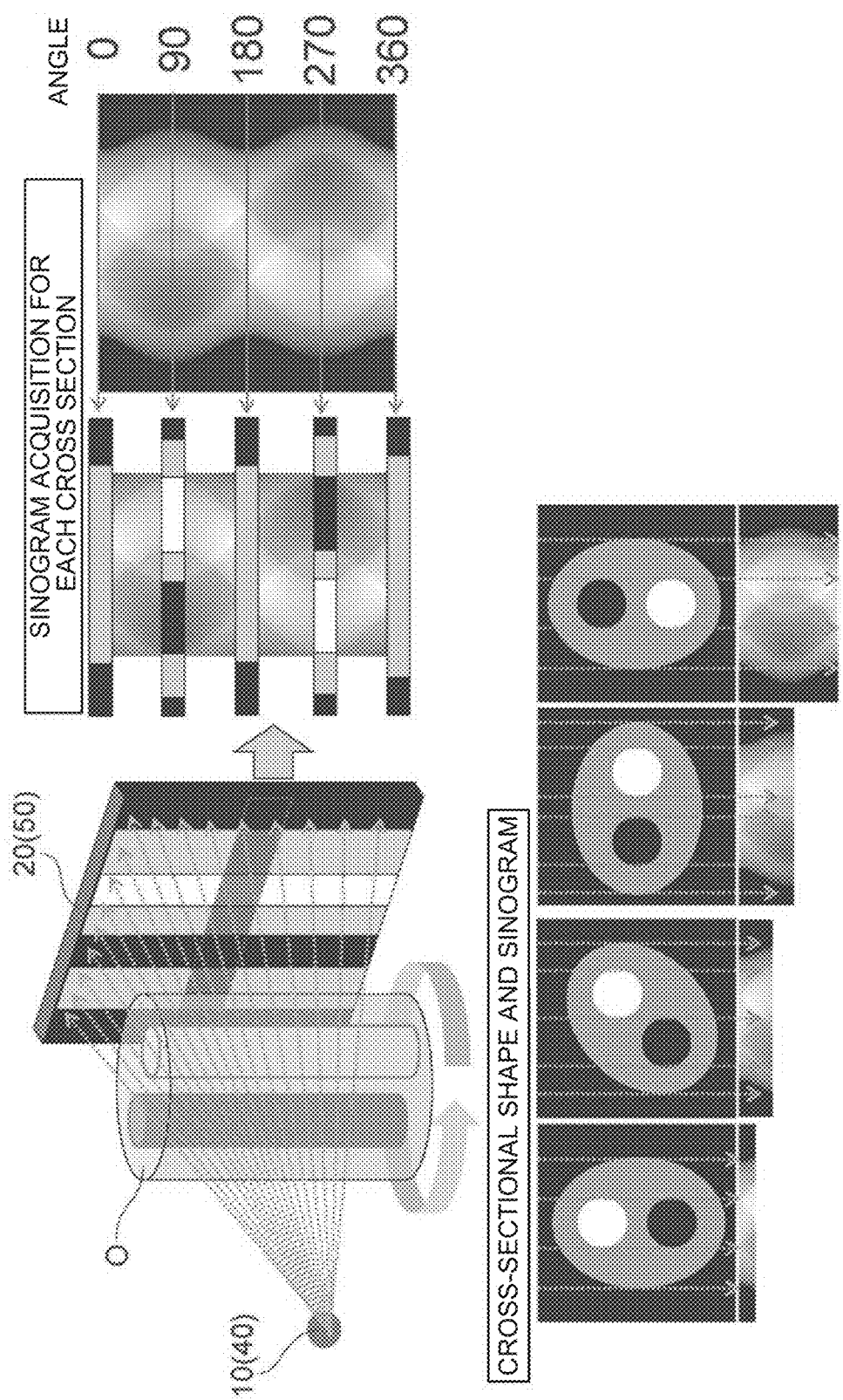
FIG. 2 is an explanatory diagram for describing a sinogram of an X-ray CT image of a measured object.

Now, the sinogram used for the image correction will be described below by using FIG. 2. FIG. 2 is an explanatory diagram for describing the sinogram of the X-ray CT image of the measured object O. The sinogram is an image, in which a detected signal is represented by a sine wave for each angle obtained by rotating the measured object O through 360 degrees, and is acquired for each cross section of the measured object O. The sinogram of the X-ray CT image (CT sinogram) on a predetermined cross section of the measured object O, having an elliptical shape on the plan view, generated by the micro image generation means 30 or the nano image generation means 60 is represented by an image as illustrated in FIG. 2, for example.

Figure 3:
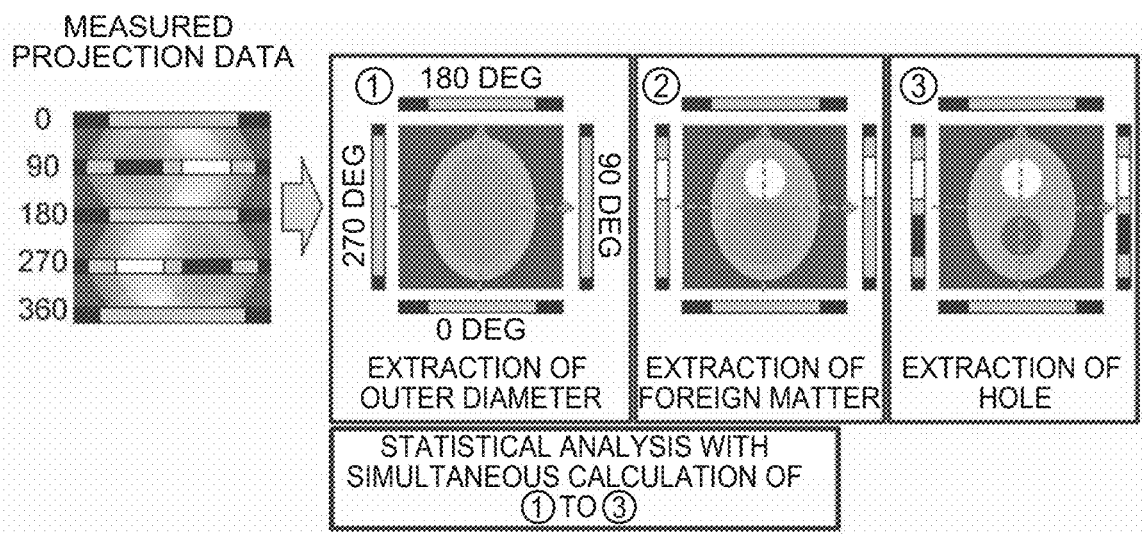
FIG. 3 is an explanatory diagram for describing a maximum likelihood estimation and expectation maximization reconstruction method.

Moreover, the ML-EM reconstruction method used for the image correction will be described by using FIG. 3 and FIG. 4. The ML-EM reconstruction method is a method of repeating calculation to find what image provides calculated projection data close to the measured projection data. As illustrated in FIG. 3, it is assumed that respective projection data (sinograms) at 0°, 90°, 180°, and 270° have been acquired. At this time, cross-sectional images acquired from these projection data can be expected. For example, an external shape is expected to be elliptical from the outermost sinogram shape. Moreover, it is suggested that a material having high luminance is present in the upper part of an ellipse and that an air layer is present in the lower part of the ellipse from the sinograms at 90° and 270°. Since there is no information on a material inside the ellipse at 180° and 270°, it is expected that the high-luminance material and the air layer cancel each other out. These manipulations are simultaneously repeated to construct a consistent cross-sectional image, and this approach outlines the ML-EM reconstruction method.

Figure 4:
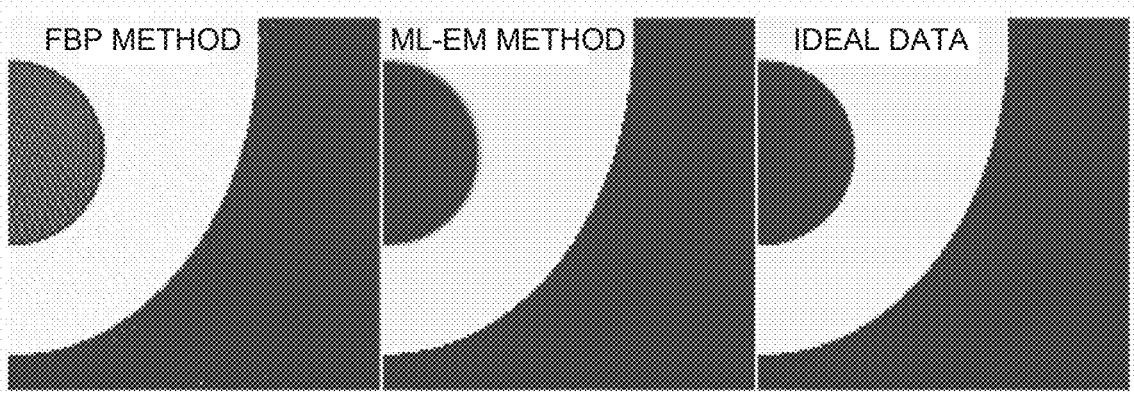
FIG. 4 is a diagram illustrating a comparison result between a cross-sectional image reconstructed by using a maximum likelihood estimation and expectation maximization reconstruction method and a cross-sectional image reconstructed by using a filtered back projection method.

FIG. 4 illustrates a comparison result between a cross-sectional image reconstructed by using the ML-EM reconstruction method and a cross-sectional image reconstructed by using the filtered back projection method (hereinafter, referred to as "FBP method"). The presence of streak-like artifacts was observed in the cross-sectional image reconstructed by the FBP method. Moreover, it was also found that the contrast differs between the hole in the inside of the sample and the air layer in the outside thereof. Meanwhile, such phenomenon has not been observed in the one reconstructed by the ML-EM method, but the blurring of the contour of the hole was observed. The FBP method is an effective reconstruction method for a sample that contains elements having significantly different linear attenuation coefficients, but less effective for artifacts attributable to complicated shapes, such as a plate shape or a shape with many projections. This is because the FBP method uses a blur correction filter in reconstruction processing. In addition, other problems occur, such as emphasized edges or uneven contrasts, due to the influences of a correction filter. These problems lead to measurement errors, and the measurement error may be more significant, depending on the shape of a measured object. Meanwhile, the ML-EM reconstruction method is capable of restraining the occurrence of artifacts manifested by the FBP method.

The ML-EM reconstruction method, however, is a method designed so as to lead to a statistically most probable image on the basis of projection data, by which it has been pointed out that the method poses the following three problems: (1) possible failure to converge because the ML-EM reconstruction method is a statistical method; (2) unclear edges of reconstructed images; and (3) an enormous volume of analysis with a resultant prolonged time required for the reconstruction. There has been a demand for developing a method that solves these problems in order to apply the ML-EM reconstruction method to practical use. The inventors of the present invention have solved the foregoing problems of the ML-EM reconstruction method by considering the sinogram acquired from a nano X-ray source image generated by using the nano X-ray source 40, which applies X-rays having a focal point size of 1 to 800 nm, to be correct and by correcting the entire image so as to converge to the sinogram.

Figure 5:
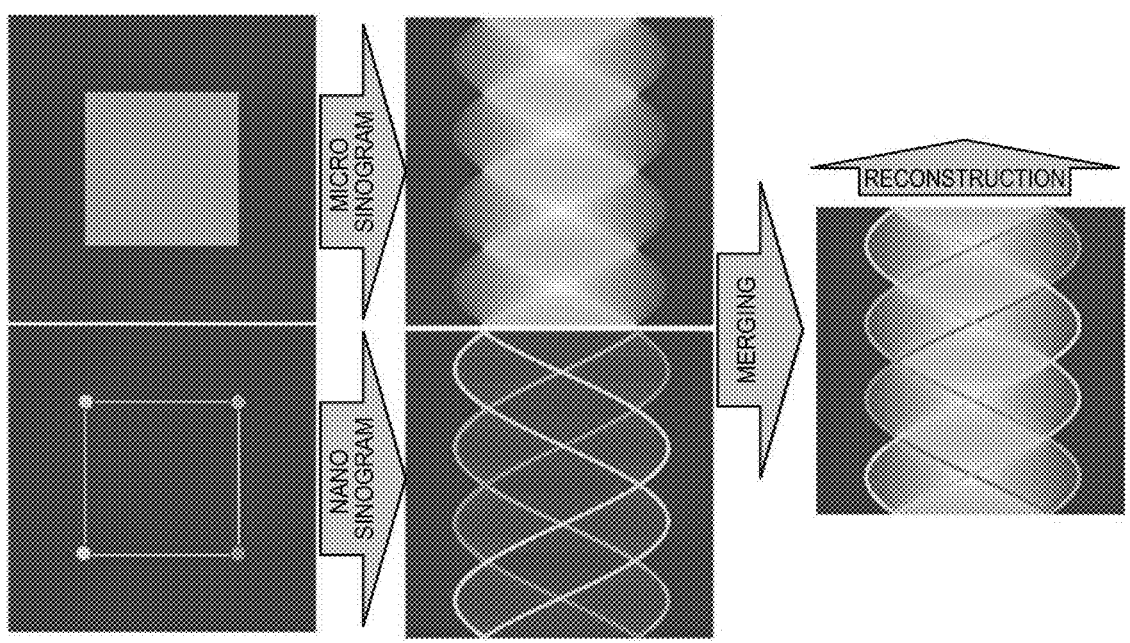
FIG. 5 is an explanatory diagram for describing a method of correcting a micro X-ray source image by using a sinogram of a nano X-ray source image.

FIG. 5 is an explanatory diagram for describing a method of correcting a micro X-ray source image by using the sinogram of a nano X-ray source image. Both of the micro X-ray source image generated by the micro image generation means 30 and the nano X-ray source image generated by the nano image generation means 60 are able to be represented by sine waves (sinograms). As illustrated in FIG. 5, the sinogram of the micro X-ray source image is very blurry and therefore the lines are relatively thick. On the other hand, the sinogram of the nano X-ray source image has been generated by using the nano X-ray source 40, which applies X-rays having a focal point size (for example, 0.25 μm) remarkably smaller than the focal point size (for example, 5 μm) of the micro X-ray source 10, by which the sinogram of the nano X-ray source image is less blur and lines thereof are thin. The sinogram of the nano X-ray source image is considered to be correct and the micro X-ray source image is reconstructed by using the ML-EM reconstruction method, by which the convergence problem and the reconstruction time problem are solved. These corrections are also applied to sinograms of the inside of the micro X-ray source image, thereby enabling the acquisition of the cross-sectional images of accurate internal and external contours.

A stage 80 is configured to rotate about a predetermined rotation axis by a moving mechanism, which is not illustrated. The stage 80 is preferably composed of granite or ductile cast iron, which has high stiffness.

In this embodiment, as illustrated in FIG. 1, the micro X-ray source 10 and the detector for the micro X-ray source 20 are arranged to be fixed on a first straight line $L_1$ passing through the center C of the stage 80, and the nano X-ray source 40 and the detector for the nano X-ray source 50 are arranged to be fixed on a second straight line $L_2$ passing through the center C of the stage 80 and intersecting with the first straight line $L_1$ at a predetermined angle θ. The image correction means 70 in this embodiment is configured to correct the micro X-ray source image generated by the micro image generation means 30 (or the nano X-ray source image generated by the nano image generation means 60) on the basis of the angle θ formed by these straight lines.

A linear scale may be arranged between the micro X-ray source 10 (the nano X-ray source 40) and the detector for the micro X-ray source 20 (the detector for the nano X-ray source 50). This makes it possible to accurately determine the position of the stage 80, so that the X-ray CT image of the measured object O is able to be accurately acquired. Moreover, the image acquisition device 1 preferably has a vibration-proof function as the measures against vibration from outside. Moreover, the image acquisition device 1 is preferably shielded by a shielding member composed of lead, tungsten, or the like, and the temperature and the humidity therein are preferably maintained constant by an air conditioning means. This enables a reduction in an influence of an external environment when acquiring image information, thereby enabling the acquisition of more accurate three-dimensional information.

Figure 6:
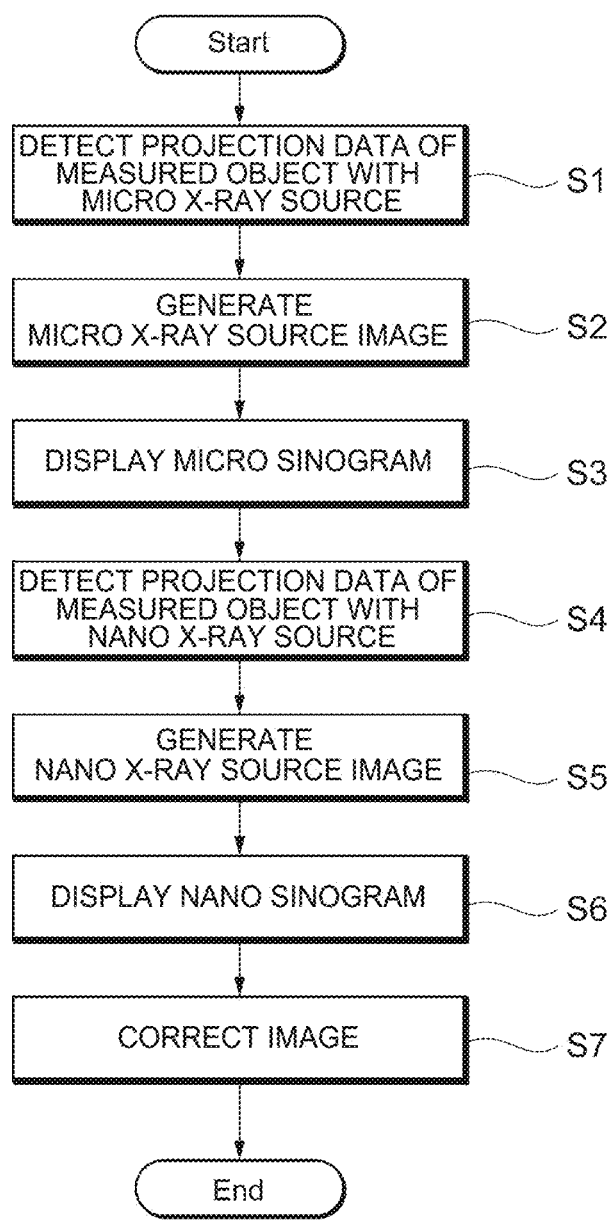
FIG. 6 is a flowchart for describing an image acquisition method according to a first embodiment of the present invention.

Subsequently, an image acquisition method with the use of the image acquisition device 1 according to this embodiment will be described by using the flowchart of FIG. 6 with appropriate reference to FIG. 5.

First, the X-rays are applied to the measured object O from the micro X-ray source 10 to detect the projection data (X-rays that have passed through the measured object O) for each rotation angle of the measured object O by the detector for the micro X-ray source 20 (a first detection step: S1), and a micro X-ray source image is generated by the micro image generation means 30 on the basis of the detected data (a first image generation step: S2). Then, the sinogram of the generated micro X-ray source image (the micro sinogram) of the measured object O is displayed on the display screen by the display means as illustrated in FIG. 5, for example (a first display step: S3).

Subsequently, X-rays are applied to the measured object O from the nano X-ray source 40 to detect the projection data (X-rays that have passed through the measured object O) for each rotation angle of the measured object O by the detector for the nano X-ray source 50 (a second detection step: S4) and a nano X-ray source image is generated by the nano image generation means 60 on the basis of the detected data (a second image generation step: S5). Then, the sinogram of the generated nano X-ray source image (the nano sinogram) of the measured object O is displayed on the display screen by the display means as illustrated in FIG. 5, for example (a second display step: S6). It is to be noted that the second detection step S4, the second image generation step S5, and the second display step S6 may be performed before the first detection step S1, the first image generation step S2, and the first display step S3.

Subsequently, the image is reconstructed by using the ML-EM reconstruction method so that the micro sinogram converges to the nano sinogram in order to correct the micro X-ray source image (an image correction step: S7). At this time, as illustrated in FIG. 5, an image obtained by merging the micro sinogram and the nano sinogram using the display means can be displayed on the display screen to reconstruct the image. Thereafter, this correction is also applied to the sinogram of the inside of the micro X-ray source image, thereby enabling the acquisition of cross-sectional images of the accurate internal and external contours.

The image acquisition device 1 according to the embodiment described above is able to correct the micro X-ray source image of the measured object O generated by using the X-rays having a relatively large focal point size of 1 μm to 1 mm on the basis of the nano X-ray source image of the measured object O generated by using the X-rays having a relatively small focal point size of 1 to 800 nm. The nano X-ray source 40 has a low transmission capability in comparison with the micro X-ray source 10 and therefore is not suitable for internal shooting of the measured object O. The nano X-ray source 40, however, provides a fluoroscopic image with clear edges, thereby enabling the acquisition of a nano X-ray source image having a highly accurate appearance shape. On the other hand, the micro X-ray source 10 has a high transmission capability in comparison with the nano X-ray source 40 and therefore is suitable for internal shooting of the measured object O. The micro X-ray source image is corrected on the basis of the nano X-ray source image having the highly accurate appearance shape and the correction is also applied to the internal data, thereby enabling the construction of highly accurate internal and external contours.

Moreover, in the image acquisition device 1 according to the embodiment described above, the micro X-ray source 10, the detector for the micro X-ray source 20, the nano X-ray source 40, and the detector for the nano X-ray source 50 are arranged to be fixed in predetermined positions, and the positions of the X-ray source and the detector do not move, thereby enabling the acquisition of a more accurate CT image.

In the above embodiments, there has been illustrated an example in which the micro X-ray source image is corrected by using the ML-EM reconstruction method. The micro X-ray source image, however, may be corrected by using a different reconstruction method (for example, a filtered back projection method, an addition type ART method, a multiplication type ART method, a SIRT method, a gradient method, a steepest descent method, a conjugate gradient method, a MAP-EM method, a convex method, or the like) by converging the micro sinogram to a nano sinogram.

Second Embodiment

Subsequently, a second embodiment of the present invention will be described by using FIGS. 7 to 10. An image acquisition device 1A according to the second embodiment is configured by modifying the configuration of the detector, the stage, and the image correction means of the image acquisition device 1 according to the first embodiment, and other components are substantially the same as those of the first embodiment. Accordingly, different components will be mainly described, while the same components as those of the first embodiment are denoted by the same reference numerals as those of the first embodiment and detailed description of the same components will be omitted hereinafter.

Figure 7:
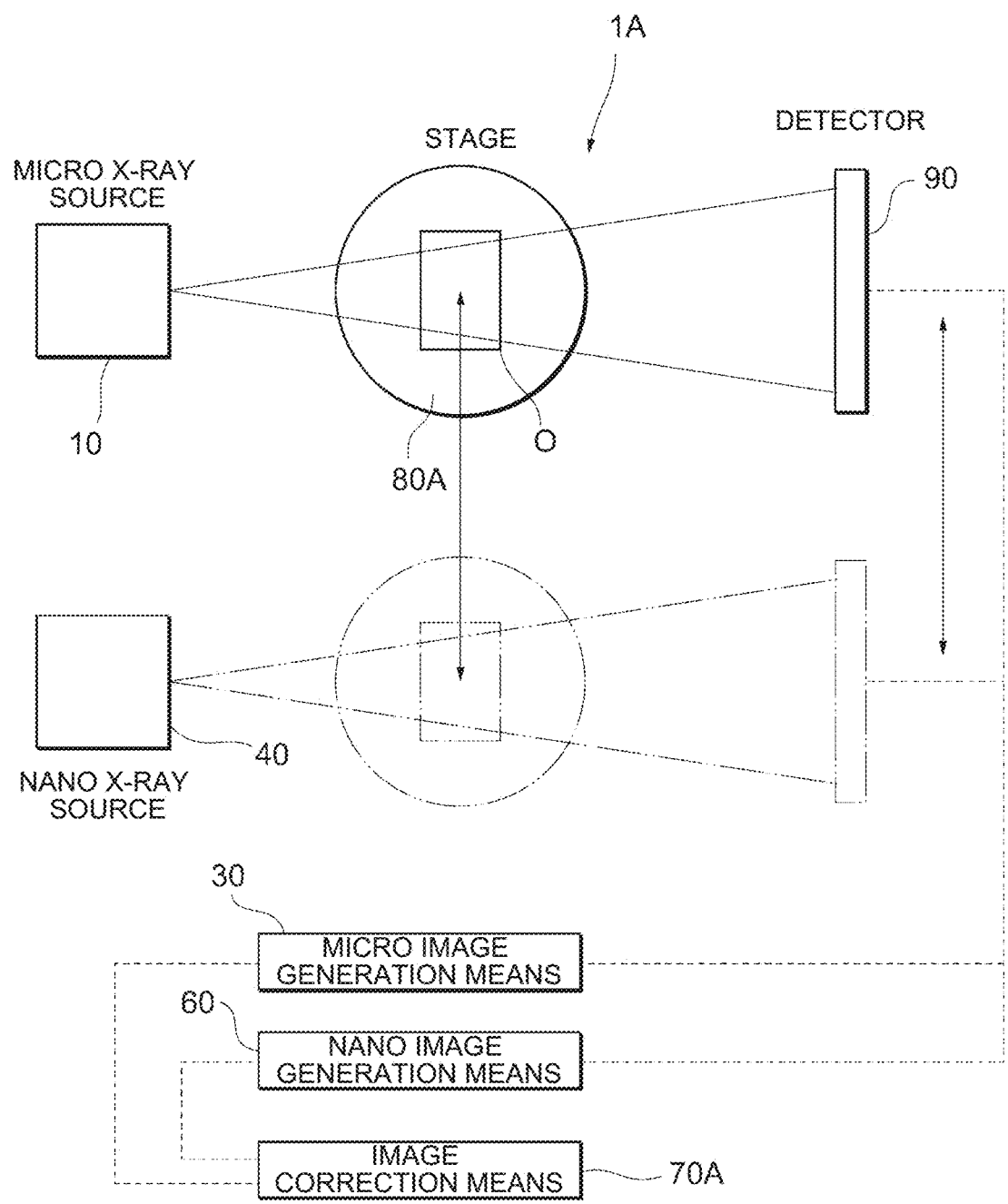
FIG. 7 is a configuration diagram for describing the configuration of an image acquisition device according to a second embodiment of the present invention.

As illustrated in FIG. 7, the image acquisition device 1A according to this embodiment includes a micro X-ray source 10, a micro image generation means 30, a nano X-ray source 40, a nano image generation means 60, an image correction means 70A, a stage 80A, and one detector 90.

The micro X-ray source 10 (a first X-ray source) and the nano X-ray source 40 (a second X-ray source) are the same as those of the first embodiment. In this embodiment, however, as illustrated in FIG. 7, the orientations of the micro X-ray source 10 and the nano X-ray source 40 are set so that the direction in which the micro X-ray source 10 applies X-rays is parallel to (does not intersect with) the direction in which the nano X-ray source 40 applies X-rays. The micro image generation means 30 (a first image generation means) and the nano image generation means 60 (a second image generation means) are also the same as those of the first embodiment and therefore detailed description thereof will be omitted here.

The detector 90 in this embodiment is configured to detect both of X-rays applied from the micro X-ray source 10 and having passed through a predetermined measured object O and X-rays applied from the nano X-ray source 40 and having passed through the measured object O, and the detector 90 corresponds to the first detector and the second detector (a common detector) in the present invention. As the detector 90, it is possible to adopt a flat panel detector, a CdTe detector, or the like.

The stage 80A in this embodiment is configured to move parallel in the horizontal direction (the direction denoted by arrows in FIG. 7) together with the detector 90 by a parallel moving mechanism, which is not illustrated. The parallel moving mechanism is used to move the stage 80A and the detector 90 between a first position that the X-rays applied from the micro X-ray source 10 reach and a second position that the X-rays applied from the nano X-ray source 40 reach and corresponds to a mounting table detector moving means in the present invention.

The image correction means 70A corrects the micro X-ray source image generated by the micro image generation means 30 on the basis of the nano X-ray source image generated by the nano image generation means 60. The image correction means 70A in this embodiment corrects the micro X-ray source image so that a difference between an edge of the micro X-ray source image generated by the micro image generation means 30 and an edge of the nano X-ray source image generated by the nano image generation means 60 falls within a predetermined range. Specifically, the image correction means 70A includes a micro image display means, which displays the micro X-ray source image of the measured object O generated by the micro image generation means 30 on a display screen, and a nano image display means, which displays the nano X-ray source image of the measured object O generated by the nano image generation means 60 on a display screen in a voxel size of the nano X-ray source image, which is smaller than the voxel size of the micro X-ray source image.

Figure 8:
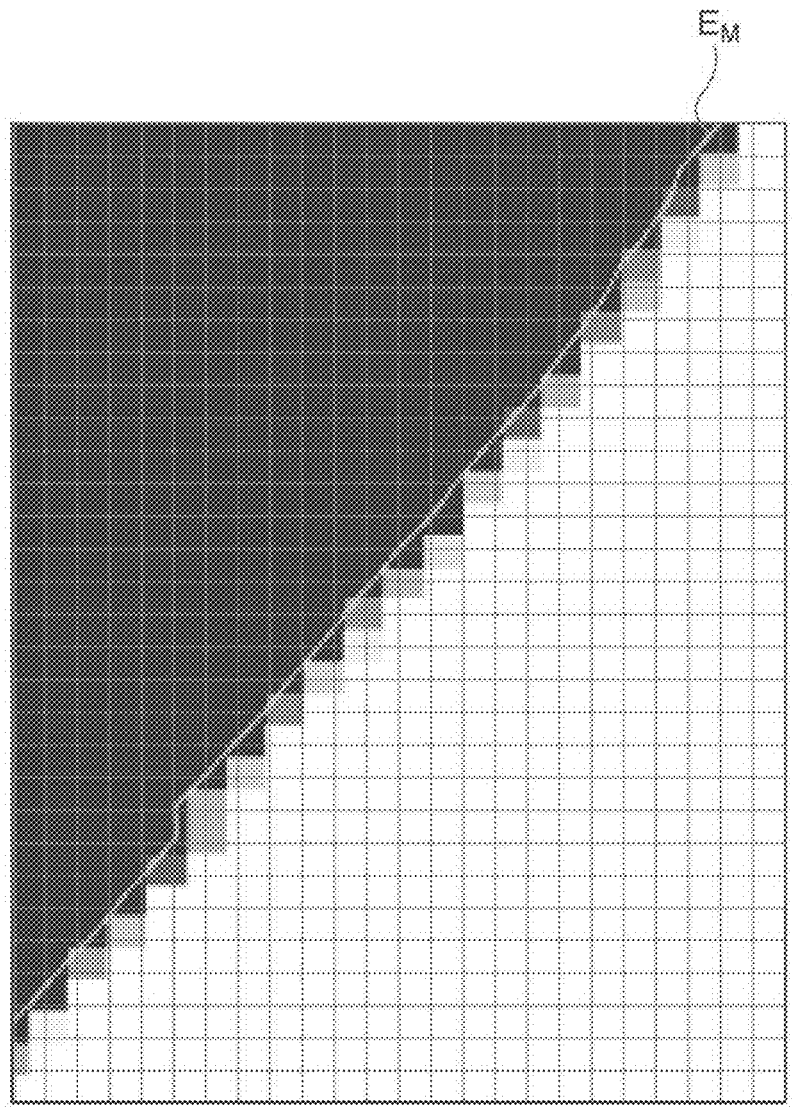
FIG. 8 is a diagram illustrating a micro X-ray source image of a measured object displayed on a display screen of the image acquisition device according to the second embodiment of the present invention.
Figure 9:
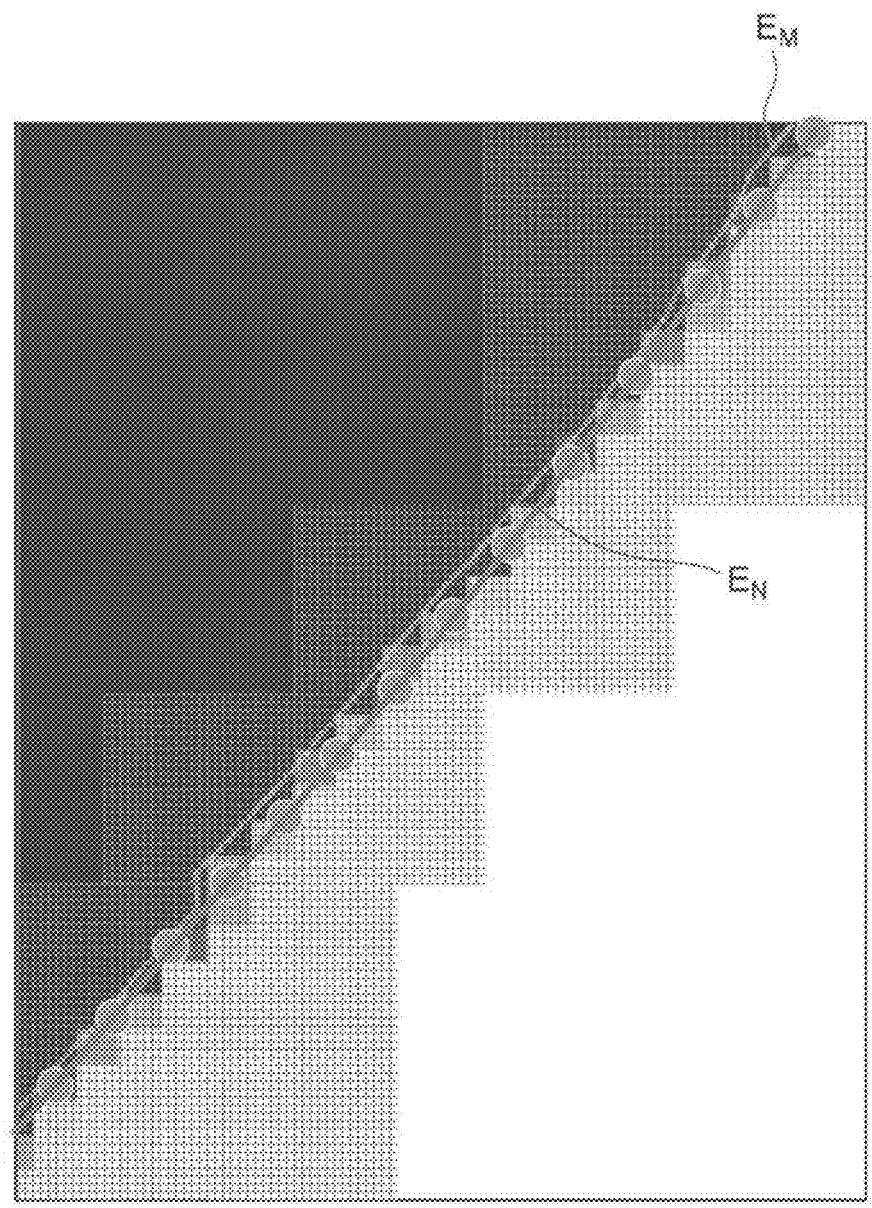
FIG. 9 is a diagram illustrating a state in which the nano X-ray source image of the measured object generated by a nano image generation means of the image acquisition device according to the second embodiment of the present invention, together with the micro X-ray source image.

FIG. 8 illustrates an edge (a micro edge) $E_M$ of the micro X-ray source image of the measured object O displayed on the display screen by the micro image display means. In this embodiment, the voxel size of the micro X-ray source image illustrated in FIG. 8 is set to 100 µm. FIG. 9 illustrates an edge (a nano edge) EN of the nano X-ray source image of the measured object O displayed on the display screen by the nano image display means. In this embodiment, the voxel size of the nano X-ray source image illustrated in FIG. 9 is set to 5 µm or so. The micro image display means and the nano image display means are also each constructed by hardware such as a computer and software such as programs installed therein. After programs for the micro image display means and the nano image display means are read into the computer, various kinds of processing is performed by an arithmetic processing unit such as a CPU, a storage unit such as a memory, and the like.

Moreover, the image correction means 70A further includes a difference calculation means, which calculates a difference between the nano edge EN and the micro edge $E_M$, and a correction means, which corrects the micro X-ray source image so that the difference calculated by the difference calculation means falls within a predetermined range. As the difference calculated by the difference calculation means, it is possible to adopt a mean square error within a specific extraction range of a distance between the nano edge EN and the micro edge $E_M$ as illustrated in FIG. 9, for example. The image correction performed by the correction means includes enlarging or reducing the micro X-ray source image, moving the micro X-ray source image in parallel in a specific direction, and rotationally moving the micro X-ray source image about a predetermined axis of rotation. As long as it is possible to minimize the difference or at least to reduce the difference to a level within a predetermined range, at least any one of the enlargement, the reduction, the parallel movement, and the rotational movement may be performed as correction. These difference calculation means and the correction means are also each constructed by hardware such as a computer and software such as programs installed therein. After programs for the difference calculation means and the correction means are read into the computer, various kinds of processing is performed by an arithmetic processing unit such as a CPU, a storage unit such as a memory, and the like.

Figure 10:
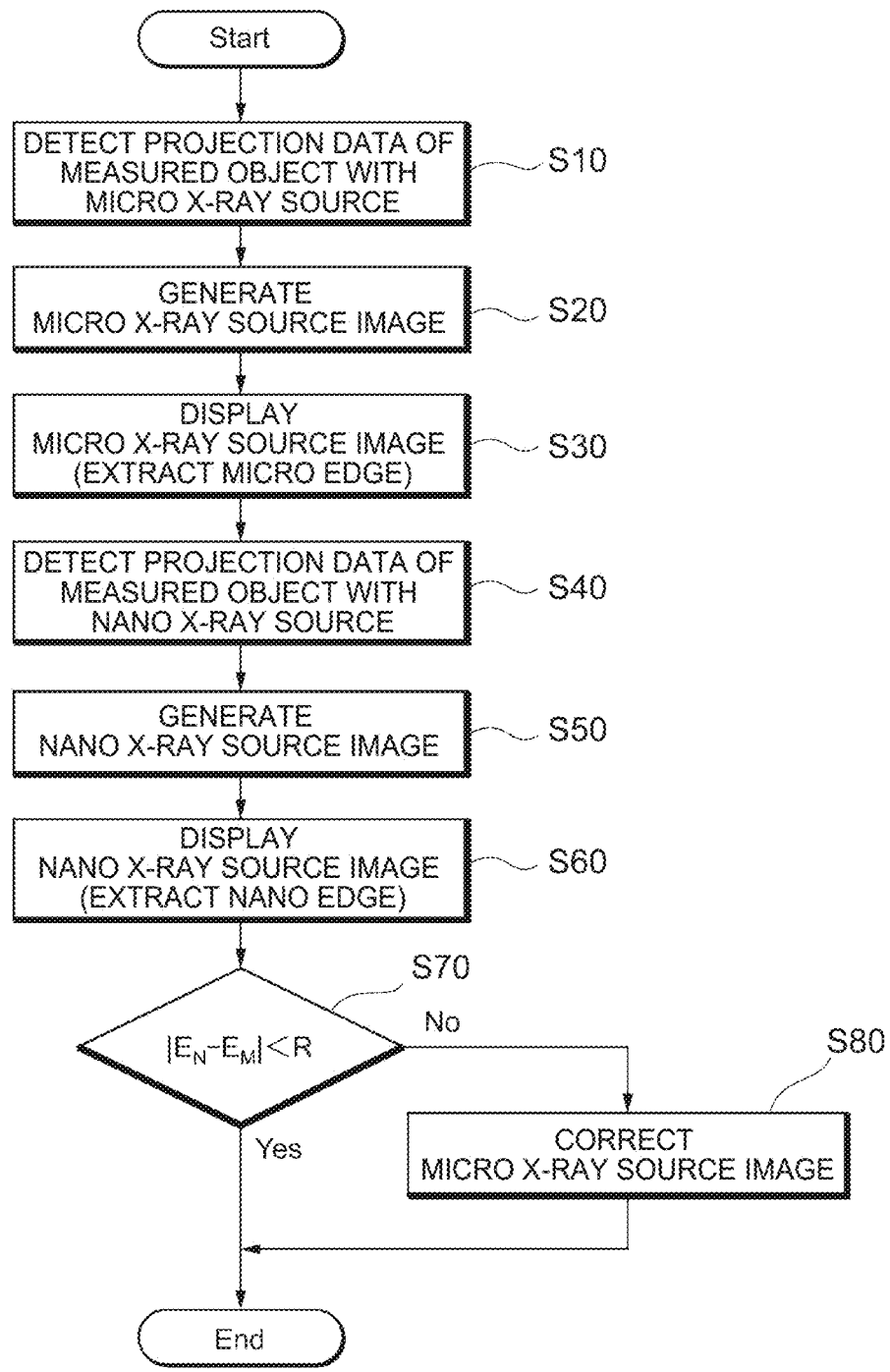
FIG. 10 is a flowchart for describing an image acquisition method according to the second embodiment of the present invention.

Subsequently, an image acquisition method using the image acquisition device 1A according to this embodiment will be described by using the flowchart of FIG. 10 with appropriate reference to FIGS. 8 and 9.

First, the X-rays are applied to the measured object O from the micro X-ray source 10 to detect the projection data (X-rays that have passed through the measured object O) for each rotation angle of the measured object O by the detector 90 (a first detection step: S10) and a micro X-ray source image is generated by the micro image generation means 30 on the basis of the detected data (a first image generation step: S20). Then, the generated micro X-ray source image of the measured object O is displayed on the display screen in a voxel size (100 µm) of the micro X-ray source image as illustrated in FIG. 8, for example, and a micro edge $E_M$ is extracted by using a conventionally-used edge extraction method (a first display step: S30).

Subsequently, X-rays are applied to the measured object O from the nano X-ray source 40 to detect the projection data (X-rays that have passed through the measured object O) for each rotation angle of the measured object O by the detector 90 (a second detection step: S40) and a nano X-ray source image is generated by the nano image generation means 60 on the basis of the detected data (a second image generation step: S50). Then, the generated nano X-ray source image of the measured object O is displayed on the display screen in the voxel size (5 μm) of the nano X-ray source image as illustrated in FIG. 9, for example, and a nano edge EN is extracted by using a conventionally-used edge extraction method (a second display step: S60). In addition, the second detection step S40, the second image generation step S50, and the second display step S60 may be performed before the first detection step S10, the first image generation step S20, and the first display step S30.

Subsequently, a difference between the micro edge $E_M$ extracted in the first display step S30 and the nano edge EN extracted in the second display step S60 is calculated and it is determined whether or not the difference falls within a predetermined range R (a difference determination step: S70). If it is determined that the difference falls within the predetermined range R in the difference determination step S70, the work is ended without correcting the micro X-ray source image. Meanwhile, if it is determined that the difference is not within the predetermined range R in the difference determination step S70, the micro X-ray source image is corrected by using the image correction means 70A (an image correction step: S80), and thereafter the correction is also applied to the sinogram of the inside of the micro X-ray source image, by which cross-sectional images of accurate internal and external contours are acquired.

The image acquisition device 1A according to the embodiment described hereinabove also provides the same operation and effect as those of the image acquisition device 1 according to the first embodiment. In other words, the image acquisition device 1A is able to correct the micro X-ray source image of the measured object O generated by using the X-rays having a relatively large focal point size of 1 μm to 1 mm on the basis of the nano X-ray source image of the measured object O generated by using the X-rays having a relatively small focal point size of 1 to 800 nm. The nano X-ray source 40 has a low transmission capability in comparison with the micro X-ray source 10 and therefore is not suitable for internal shooting of the measured object O. The nano X-ray source 40, however, provides a fluoroscopic image with clear edges, thereby enabling the acquisition of a nano X-ray source image having a highly accurate appearance shape. On the other hand, the micro X-ray source 10 has a high transmission capability in comparison with the nano X-ray source 40 and therefore is suitable for internal shooting of the measured object O. The micro X-ray source image is corrected on the basis of the nano X-ray source image having a highly accurate appearance shape, and the correction is also applied to the internal data, thereby enabling the construction of a highly accurate internal and external contours.

Moreover, the image acquisition device 1A according to the embodiment as described above uses the detector 90, which detects both of the X-rays applied from the micro X-ray source 10 and having passed through the predetermined measured object O and the X-rays applied from the nano X-ray source 40 and having passed through the measured object O, and therefore there is no need to prepare two detectors. This leads to cost reduction.

Third Embodiment

Subsequently, a third embodiment of the present invention will be described by using FIGS. 11 and 12. An image acquisition device 1B according to the third embodiment is configured by modifying the configuration of the X-ray source, the detector, and the stage of the image acquisition device 1A according to the second embodiment and other components are substantially the same as those of the second embodiment. Accordingly, different components will be mainly described, while the same components as those of the second embodiment are denoted by the same reference numerals as those of the second embodiment and detailed description of the same components will be omitted hereinafter.

Figure 11:
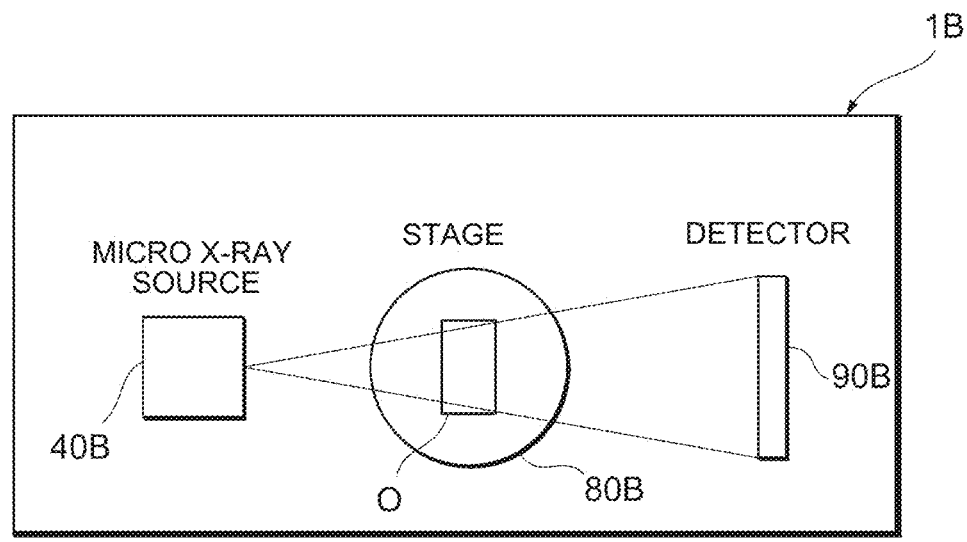
FIG. 11 is a top view of an image acquisition device according to a third embodiment of the present invention.
Figure 12:
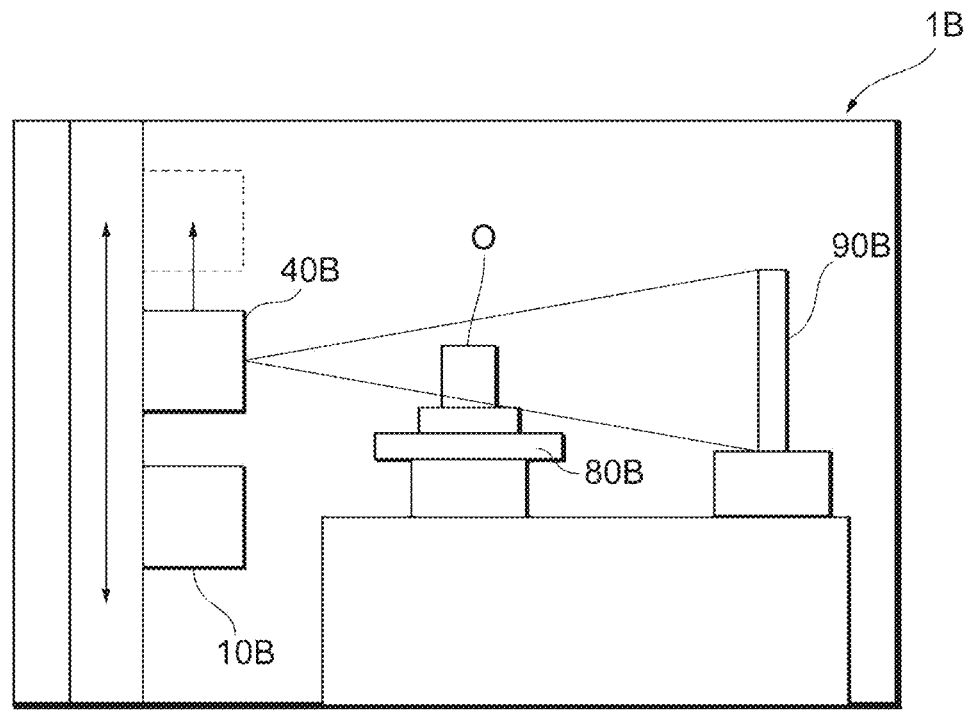
FIG. 12 is a side view of the image acquisition device according to the third embodiment of the present invention.

As illustrated in FIGS. 11 and 12, the image acquisition device 1B according to this embodiment includes a micro X-ray source 10B, a nano X-ray source 40B, a stage 80B, a detector 90B, a micro image generation means, a nano image generation means, and an image correction means. The micro image generation means (a first image generation means), the nano image generation means (a second image generation means), and the image correction means are the same as those of the second embodiment, and therefore the illustrations and detailed description thereof will be omitted here.

Regarding the micro X-ray source 10B (a first X-ray source) and the nano X-ray source 40B (a second X-ray source) in this embodiment, similarly to the second embodiment, the orientations of the micro X-ray source 10B and the nano X-ray source 40B are set so that the direction in which the micro X-ray source 10B applies X-rays is parallel to (does not intersect with) the direction in which the nano X-ray source 40B applies X-rays. In this embodiment, however, as illustrated in FIG. 12, the nano X-ray source 40B is arranged vertically below the micro X-ray source 10B. Furthermore, the micro X-ray source 10B and the nano X-ray source 40B are configured to move parallel in the vertical direction (the direction denoted by arrows in FIG. 12) by a parallel moving mechanism, which is not illustrated. The parallel moving mechanism vertically moves the micro X-ray source 10B and the nano X-ray source 40B so that the X-rays are applied from the micro X-ray source 10B and from the nano X-ray source 40B separately to the measured object O mounted on the stage 80B. The parallel moving mechanism corresponds to an X-ray source moving means of the present invention.

The basic functions of the detector 90B (a first detector and a second detector) in this embodiment are the same as those of the second embodiment. Thus, the detector 90B detects both of the X-rays applied from the micro X-ray source 10B and having passed through a predetermined measured object O and the X-rays applied from the nano X-ray source 40B and having passed through the measured object O. The stage 80B and the detector 90B in this embodiment are arranged to be fixed in predetermined respective positions.

The image acquisition device 1B according to this embodiment as described hereinabove also provides the same operation and effect as those of the image acquisition devices according to the first and second embodiments. Moreover, in the image acquisition device 1B according to the embodiment described above, there is no need to move the stage 80B and the detector 90B to right and left (in the horizontal direction), thereby enabling a reduction in size of the entire device advantageously.

The invention is not limited to the above-described embodiments, and appropriate modifications of the embodiments in design made by a person skilled in the art are also included in the scope of the invention as long as these have the characteristics of the invention. That is, the respective elements of the embodiments, and positions, materials, conditions, shapes, sizes, and the like thereof are not limited to the examples and may be appropriately modified. In addition, the respective elements of the embodiments may be combined as long as the combination is technically possible, and combinations of the elements are also included in the scope of the invention as long as these have the characteristics of the invention.

REFERENCE SIGNS LIST 1, 1A, 1B: image acquisition device
10, 10B: micro X-ray source (first X-ray source)
20: detector for micro X-ray source (first detector)
30: micro image generation means (first image generation means)
40, 40B: nano X-ray source (second X-ray source)
50: detector for nano X-ray source (second detector)
60: nano image generation means (second image generation means)
70: image correction means
80, 80A, 80B: stage (mounting table)
90, 90B: detector (first detector, second detector)
O: measured object
S1, S10: first detection step
S2, S20: first image generation step
S4, S40: second detection step
S5, S50: second image generation step
S7, S80: image correction step

What is claimed is:

1. An image acquisition device comprising:
a first X-ray source that applies X-rays having a first focal point size;
a first detector that detects X-rays applied from the first X-ray source and having passed through a measured object;
a first image generation means that generates a first X-ray CT image, based on the X-rays detected by the first detector;
a second X-ray source that applies X-rays having a second focal point size smaller than the first focal point size;
a second detector that detects the X-rays applied from the second X-ray source and having passed through the measured object;
a second image generation means that generates a second X-ray CT image, based on the X-rays detected by the second detector; and
an image correction means that corrects the first X-ray CT image generated by the first image generation means, based on the second X-ray CT image generated by the second image generation means, so that a difference between an edge of the first X-ray CT image generated by the first image generation means and an edge of the second X-ray CT image generated by the second image generation means falls within a predetermined range.

2. The image acquisition device according to claim 1, further comprising an X-ray source moving means that moves the first X-ray source and the second X-ray source up and down so that X-rays are applied to the measured object from the first X-ray source and from the second X-ray source separately.

3. An image acquisition device comprising:
a first X-ray source that applies X-rays having a first focal point size;
a first detector that detects X-rays applied from the first X-ray source and having passed through a measured object, wherein the first X-ray source and the first detector are arranged to be fixed on a first straight line passing through the center of a mounting table on which the measured object is mounted;
a first image generation means that generates a first X-ray CT image, based on the X-rays detected by the first detector;
a second X-ray source that applies X-rays having a second focal point size smaller than the first focal point size;
a second detector that detects the X-rays applied from the second X-ray source and having passed through the measured object, wherein the second X-ray source and the second detector are arranged to be fixed on a second straight line passing through the center of the mounting table and intersecting with the first straight line at a predetermined angle;
a second image generation means that generates a second X-ray CT image, based on the X-rays detected by the second detector; and
an image correction means that corrects the first X-ray CT image generated by the first image generation means, based on the second X-ray CT image generated by the second image generation means, and corrects at least one of the first X-ray CT image generated by the first image generation means and the second X-ray CT image generated by the second image generation means, based on the predetermined angle.

4. An image acquisition device comprising:
a first X-ray source that applies X-rays having a first focal point size;
a first detector that detects X-rays applied from the first X-ray source and having passed through a measured object;
a first image generation means that generates a first X-ray CT image, based on the X-rays detected by the first detector;
a second X-ray source that applies X-rays having a second focal point size smaller than the first focal point size;
a second detector that detects the X-rays applied from the second X-ray source and having passed through the measured object, where the first detector and the second detector are a common detector;
a mounting table detector moving means that moves a mounting table on which the measured object is mounted and the common detector between a first position where the X-rays applied from the first X-ray source reach and a second position where the X-rays applied from the second X-ray source reach;
a second image generation means that generates a second X-ray CT image, based on the X-rays detected by the second detector; and
an image correction means that corrects the first X-ray CT image generated by the first image generation means, based on the second X-ray CT image generated by the second image generation means.

5. An image acquisition method comprising:
a first detection step of detecting X-rays applied from a first X-ray source, which applies X-rays having a first focal point size, and having passed through a measured object;
a first image generation step of generating a first X-ray CT image, based on the X-rays detected in the first detection step;
a second detection step of detecting X-rays applied from a second X-ray source, which applies X-rays having a second focal point size smaller than the first focal point size, and having passed through the measured object;

a second image generation step of generating a second X-ray CT image, based on the X-rays detected in the second detection step; and an image correction step of correcting the first X-ray CT image generated in the first image generation step, based on the second X-ray CT image generated in the second image generation step, so that a difference between an edge of the first X-ray CT image generated in the first image generation step and an edge of the second X-ray CT image generated in the second image generation step falls within a predetermined range.

6. An image correction program causing a computer to perform an image correction step of correcting a first X-ray CT image generated based on X-rays applied from a first X-ray source so that a difference between an edge of the first X-ray CT image and an edge of a second X-ray CT image falls within a predetermined range, which applies X-rays having a first focal point size, and having passed through a measured object, based on the second X-ray CT image that is generated based on X-rays applied from a second X-ray source, which applies X-rays having a second focal point size smaller than the first focal point size, and having passed through the measured object.

\* \* \* \* \*